United States Patent [19]
Wei et al.

[11] Patent Number: 5,723,420
[45] Date of Patent: Mar. 3, 1998

[54] PERSONAL CLEANSING BAR COMPOSITIONS WHICH CONTAIN A FRAGRANCE-RELEASING COMPLEX FOR IMPROVED FRAGRANCE DELIVERY

[75] Inventors: Karl Shiqing Wei; Louis Fay Wong, both of Mason; Deborah Adamo Koehler, Middletown; Mark Richard Sine, Morrow, all of Ohio

[73] Assignee: The Procter & Gamble Company, Cincinnati, Ohio

[21] Appl. No.: 610,689

[22] Filed: Mar. 4, 1996

[51] Int. Cl.[6] ............................. C11D 3/50
[52] U.S. Cl. ............. 510/101; 510/102; 510/152; 510/294; 510/347; 510/349; 510/440
[58] Field of Search ................... 510/101, 102, 510/152, 294, 347, 349, 440; 512/4

[56] References Cited

U.S. PATENT DOCUMENTS

| | | | |
|---|---|---|---|
| 4,443,362 | 4/1984 | Gath et al. | 510/126 X |
| 4,511,513 | 4/1985 | Gath et al. | 510/123 X |
| 4,954,285 | 9/1990 | Wierenga et al. | 252/174.11 |
| 5,137,646 | 8/1992 | Schmidt et al. | 510/101 X |
| 5,154,842 | 10/1992 | Walleg et al. | 510/101 X |
| 5,188,753 | 2/1993 | Schmidt et al. | 510/101 X |
| 5,336,665 | 8/1994 | Garner-Gray | 512/4 |
| 5,500,154 | 3/1996 | Bacon et al. | 510/102 |
| 5,501,805 | 3/1996 | Becher et al. | 510/102 |

FOREIGN PATENT DOCUMENTS

| | | |
|---|---|---|
| WO 94/16046 | 7/1994 | WIPO . |
| WO 94/19449 | 9/1994 | WIPO . |

*Primary Examiner*—Michael Lusignan
*Attorney, Agent, or Firm*—Tara M. Rosnell

[57] ABSTRACT

Personal cleansing bar compositions which contain a fragrance-releasing complex and a bar carrier. The fragrance-releasing complex contains a hydrophilic inorganic porous fragrance carrier and a fragrance impregnated within the fragrance carrier. The ratio of the fragrance:fragrance carrier ranges from about 5:1 to about 1:10.

20 Claims, No Drawings

PERSONAL CLEANSING BAR COMPOSITIONS WHICH CONTAIN A FRAGRANCE-RELEASING COMPLEX FOR IMPROVED FRAGRANCE DELIVERY

TECHNICAL FIELD

This invention relates to personal cleansing bar compositions which contain hydrophilic inorganic fragrance carders. The personal cleansing bars of the present invention can provide improved fragrance stability, enhanced in-use fragrance bloom, and dual fragrance delivery.

BACKGROUND OF THE INVENTION

The present invention relates to personal cleansing bar compositions having improved fragrance delivery. The improved fragrance delivery is achieved via fragrance carrier systems employed in the personal cleansing bars. Fragrances, e.g., perfumes, are a desirable part of personal cleansing products for two main reasons: they cover up the unpleasant raw material malodors; and they provide an olfactory aesthetic benefit. Fragrances are also used in personal cleansing products to serve as a signal that the product is effective (e.g., that the skin is clean and fresh).

Fragrances such as perfumes are often added directly to base soap compositions. There are, however, several disadvantages when perfumes are mixed as neat oil in the products. One problem is that some perfume ingredients are not stable in the soap matrix and thus are subject to damage and/or loss. They can also undergo an oxidative or other chemical reaction (e.g., by oxygen, light, heat etc.) and cause undesired discoloration of the products containing them.

A further disadvantage arising from the direct addition of perfumes to base soap compositions is that perfume components are, in general, volatile and, therefore, easily lost from the product during processing or storage. The loss of the highly volatile fraction of the perfume is especially high. As a result, in the past, personal cleansing bars tended to employ perfumes composed mainly of less volatile, high boiling (having high boiling points), perfume components to maximize survival of the fragrance during processing and storage of the bar and thus provide better in-use and after-use fragrance benefits. This was not the most desirable situation, however, because some of the volatile, low boiling perfume ingredients can provide a fresh and clean impression, and it is highly desirable that these ingredients be delivered and present in the personal cleansing product.

Another problem arising from the direct addition of perfume to base soap compositions is that there is no flexibility to simultaneously optimize fragrance display in the neat product (e.g., the bar) and during use of the product. For example, the optimum fragrance level during use may result in the neat product smelling too strong. Likewise, the optimum fragrance level in the bar may lead to less satisfactory results during use. It would be desirable to be able to adjust the fragrance display independently in the neat product and in use.

Perfumes are ingredients that have commonly been added to personal cleansing compositions to impart aesthetically attractive aromas, as mentioned hereinbefore. Perfumes can be designed and selected to make a variety of impressions on the user. Unfortunately, any particular perfume will typically convey only a single or continuous overall message, and would not clearly communicate the multiple functions of a multiple function cleansing product or be enhanced during the products usage to reinforce the performance of the product. Therefore, it is highly desirable that a dual fragrance characters be delivered in the personal cleansing bars to convey the distinctiveness of the product or multiple, distinct functions of the product.

Others have attempted to provide improved fragrance delivery. For example, U.S. Pat. No. 5,336,665 to Garner-Gray et al. issued Aug. 9, 1994 discloses fragrance complexes using a hydrophobic inorganic carrier for deposition. However, these carders cannot release the majority of perfume during the washing process.

It is known in the food industry to put flavors onto silica gel particles to form dry, flowable flavor powders. Flavor oil to silica gel ratios of up to 3:1 can be used. When the particles are added to water, the flavor is released.

The present inventors have found that the use of certain hydrophllic inorganic perfume carders to deliver perfumes in personal cleansing bars provides improved fragrance stability of the bar containing the perfume, enhances in-use fragrance bloom of the bar, and can provide dual fragrance delivery for the bar. It is therefore an object of the present invention to provide such personal cleansing compositions.

SUMMARY OF THE INVENTION

A personal cleansing bar composition comprising:

a) from about 0.1% to about 20% of a fragrance releasing complex comprising:
  i) from about 10% to about 90% of a hydrophilic inorganic porous fragrance carrier; and
  ii) from about 10% to about 90% of a fragrance impregnated within said carrier, wherein the ratio of fragrance::fragrance carrier ranges from about 5:1 to about 1:10; and b) from about 80% to about 99.9% of a bar carrier.

DETAILED DESCRIPTION OF THE INVENTION

The present invention is directed to personal cleansing compositions which are stable and which deliver fragrances in an efficient, cost-effective and unique manner. In particular, the personal cleansing bar compositions of the present invention can convey dual fragrance characteristics and can exhibit desirable fragrance characteristics in their neat (e.g., dry) form as well as during use. The personal cleansing compositions of the present invention comprise a fragrance-releasing complex and a bar carrier. The fragrance-releasing complex and the bar carrier are described in detail as follows:

I. Fragrance-releasing complex

The personal cleansing bar compositions of the present invention comprise from about 0.1% to about 20%, preferably from about 0.2% to about 10%, most preferably from about 0.5% to about 5% of a fragrance-releasing complex. The fragrance-releasing complex comprises a hydrophilic inorganic porous fragrance carrier and a fragrance which is impregnated within the fragrance carrier.

The ratio of the fragrance to the fragrance carrier within the fragrance-releasing complex typically ranges from about 5:1 to about 1:10, preferably from about 5:1 to about 1:2, more preferably from about 2:1 to about 1:2, depending on the absorbency of the fragrance carrier. When a fragrance carrier with a high absorbency is used, the ratio of fragrance::fragrance carrier is about 5:1. When a carrier of low absorbency is used, the ratio of fragrance:fragrance carrier is about 1:10. For fragrance carriers with moderate absorbencies, the ratio of fragrance:fragrance carrier lies between 5:1 and 1:10. Some typical ratios of fragrance:fragrance carrier for certain key fragrance carriers are listed in the table below:

| Fragrance Carrier | Ratio Fragrance:Fragrance Carrier |
|---|---|
| Silica | 2:1 |
| Zeolite | 1:6 |
| β-Cyclodextrin | 1:6 |

A. The Fragrance

The fragrance-releasing complex comprising the personal cleansing bar compositions of the present invention comprises from about 10% to about 90%, preferably from about 15% to about 80%, more preferably from about 40% to about 70% of a fragrance. As used herein, the term "fragrance" can include perfume ingredients, cooling agents and other tactile agents, or a combination thereof.

The perfume ingredients employed in the personal cleansing compositions of the present invention are the conventional ones known in the art. Even perfume ingredients which are unstable due to volatility (as exhibited by changes in intensity) or discoloration when used in their neat form are stable and suitable for use in the personal cleansing bar compositions of the present invention when they are impregnated in a fragrance carrier as hereinafter described. As used herein, a fragrance is considered to be "stable" if the fragrance does not exhibit appreciable changes in color or intensity and does not exhibit appreciable loss due to volatility after 10 days at 120° F.

Suitable perfume compounds and compositions can be found in the art including U.S. Pat. No. : 4,145,184, Brain and Cummins, issued Mar. 20, 1979; U.S. Pat. No. 4,209,417, Whyte, issued Jun. 24, 1980; U.S. Pat. No. 4,515,705, Moeddel, issued May 7, 1985; and U.S. Pat. No. 4,152,272, Young, issued May 1, 1979, all of said patents being incorporated herein by reference.

Perfumes can be classified according to their volatility. The highly volatile, low boiling, perfume ingredients typically have boiling points of about 250° C. or lower. The moderately volatile perfume ingredients are those having boiling points of from about 250° C. to about 300° C. The less volatile, high boiling, perfume ingredients are those having boiling points of about 300° C. or higher. Many of the perfume ingredients as discussed hereinafter, along with their odor and/or flavor characters, and their physical and chemical properties, such as boiling point and molecular weight, are given in "Perfume and Flavor Chemicals (Aroma Chemicals)," Steffen Arctander, published by the author, 1969, incorporated herein by reference.

Examples of the highly volatile, low boiling, perfume ingredients are: anethole, benzaldehyde, benzyl acetate, benzyl alcohol, benzyl formate, iso-bornyl acetate, camphene, cis-citral (neral), citronellal, citronellol, citronellyl acetate, para-cymene, decanal, dihydrolinalool, dihydromyrcenol, dimethyl phenyl carbinol, eucalyptol, geranial, geraniol, geranyl acetate, geranyl nitrile, cis-3-hexenyl acetate, hydroxycitronellal, d-limonene, linalool, linalool oxide, linalyl acetate, linalyl propionate, methyl anthranilate, alpha-methyl ionone, methyl nonyl acetaldehyde, methyl phenyl carbinyl acetate, laevo-menthyl acetate, menthone, iso-menthone, myrcene, myrcenyl acetate, myrcenol, nerol, neryl acetate, nonyl acetate, phenyl ethyl alcohol, alpha-pinene, beta-pinene, gamma-terpinene, alpha-terpineol, beta-terpineol, terpinyl acetate, and vertenex (para-tertiary-butyl cyclohexyl acetate). Some natural oils also contain large percentages of highly volatile perfume ingredients. For example, lavandin contains as major components: linalool; linalyl acetate; geraniol; and citronellol. Lemon oil and orange terpenes both contain about 95% of d-limonene.

Examples of moderately volatile perfume ingredients are: amyl cinnamic aldehyde, iso-amyl salicylate, beta-caryophyllene, cedrene, cinnamic alcohol, coumarin, dimethyl benzyl carbinyl acetate, ethyl vanillin, eugenol, iso-eugenol, flor acetate, heliotropine, 3-cis-hexenyl salicylate, hexyl salicylate, lilial (para-tertiarybutyl-alpha-methyl hydrocinnamic aldehyde), gamma-methyl ionone, nerolidol, patchouli alcohol, phenyl hexanol, beta-selinene, trichloromethyl phenyl carbinyl acetate, triethyl citrate, vanilla and veratraldehyde. Cedarwood terpenes are composed mainly of alpha-cedrene, beta-cedrene, and other $C_{15}H_{24}$ sesquiterpenes.

Examples of the less volatile, high boiling, perfume ingredients are: benzophenone, benzyl salicylate, ethylene brassylate, galaxolide (1,3,4,6,7,8-hexahydro-4,6,6,7,8,8-hexamethyl-cyclopenta-gama-2-benzopyran), hexyl cinnamic aldehyde, lyral (4-(4-hydroxy-4-methyl pentyl)-3-cyclohexene-10-carboxaldehyde), methyl cedrylone, methyl dihydro jasmonate, methyl-beta-naphthyl ketone, musk indanone, musk ketone, musk tibetene, and phenylethyl phenyl acetate.

As hereinbefore indicated, the fragrance employed in the personal cleansing bar compositions of the present invention can also comprise a cooling agent or a combination of cooling agents. Cooling agents are compounds which directly effect those nerve endings responsible for hot or cold sensations. Suitable cooling agents are menthol, menthol-based or acyclic carboximides, and menthol-based or acyclic ketals (acetals). The cooling agents particularly preferred for use in the personal cleansing bar compositions of the present invention are those selected from the group consisting of 3-1-menthoxy propane-1,2-diol, N-substituted-p-menthane-3-carboxamides and acyclic carboxamides and mixtures thereof.

3-1-menthoxy propane 1,2-diol is fully described in detail in U.S. Pat. No. 4,459,425, issued Jul. 10, 1984 to Amano et. al, incorporated herein by reference in its entirety. This volatile aromatic is commercially available, as TK-10 from Takasago Perfumery Co., Ltd., Tokyo, Japan.

The N-substituted-p-menthane-3-carboxamides are fully described in U.S. Pat. No. 4,136,163 to Watson et al., issued Jan. 23, 1979 incorporated herein by reference in its entirety. The most preferred cooling agent of this class is N-ethyl-p-menthane-3-carboxamide which is commercially available as WS-3 from Wilkinson Sword Limited.

Useful acyclic carboxamides are fully described in U.S. Pat. No. 4,230,688 to Rowsell et al., issued Oct. 28 1980 incorporated herein by reference in its entirety. The most preferred cooling agent of this class is N,2,3-trimethyl-2-isopropylbutanamide which is commercially available as WS-23 from Wilkinson Sword Limited.

Preferred for use herein is a mixture of 3-1-menthoxy propane 1,2-diol, N-ethyl-p-menthane-3-carboxamide and N,2,3-trimethyl-2-isopropylbutanamide in a ratio of 1:75:42, respectively.

B. The Fragrance Carrier

The fragrance-releasing complex employed in the personal cleansing bar compositions of the present invention also comprises from about 10% to about 90%, preferably from about 20%, to about 85%, more preferably from about 30% to about 60% of a hydrophilic inorganic porous fragrance carrier. The fragrance carrier is typically present in the personal cleansing bar compositions of the present invention at a level ranging from about 0.01% to about 10%, preferably from about 0.1% to about 5%, more preferably from about 0.2% to about 2%. The perfume carriers improve fragrance delivery. By "improving fragrance delivery" is meant that the fragrance stability and in-use fragrance bloom are improved and further that the composition can deliver a novel dual fragrance character in personal cleansing bars.

The fragrance carriers employed in the personal cleansing bar compositions of the present invention comprise hydrophilic particles having a diameter of from about 0.001 micron to about 50 microns, preferably from about 0.01 to about 20 microns, more preferably from about 0.1 to about 10 microns. As used herein, a "hydrophilic carrier particle" means a particle which entraps a fragrance (e.g. perfume oil) in the dry (e.g., neat) personal cleansing bar composition product and releases entrapped fragrance when the product gets wet. A carrier is hydrophilic for purposes herein if the carrier passes either one of the two hydrophilicity tests hereinafter described in the Methods section.

One type of inorganic carriers suitable for use in the present invention include amorphous silica, precipitated silica, fumed silica and aluminosilicates such as zeolite and alumina with a pore volume of at least 0.1 ml/g consisting of pores with a diameter between 4 and 100 A, which by their nature are hydrophilic. Preferably, amorphous Silica gel is used because of its high oil absorbency. Silica gel particles include SyloidR silicas such as Numbers: 72; 74; 221; 234; 235; 244; etc. SyloidR silicas are available from W. R. Grace & Co., Davison Chemical Division, P.O. Box 2117, Baltimore, Md. 21203. Such particles have surface areas of from about 250 to about 340 m$^2$/g; pore volumes of from about 1.1 to about 1.7 cc/g; and average particle sizes of from about 2.5 to about 6 microns. Fumed silica particles have primary particle diameters of from about 0.007 to about 0.025 micron and include Cab-O-SilR Numbers: L-90; LM-130; LM-5; M-5; PTG; MS-55; HS-5; and EH-5. Cab-O-SilR silicas are available from Cabot Corp., P.O. Box 188, Tuscola, Ill. 61953. It is preferred that there be only minimal amounts of other materials present when the perfume is added to the silica particles to maximize adsorption. It is especially preferred that only small amounts, e.g., less than about 10% of organic materials, including waxes, be present.

Another type of inorganic carrier suitable for use in the present invention include cyclodextrin. As used herein, the term "cyclodextrin" (CD) includes any of the known cyclodextrins such as unsubstituted cyclodextrins containing from six to twelve glucose units, especially, alpha-, beta-, gamma-cyclodextrins, and mixtures thereof, and/or their derivatives, and/or mixtures thereof, that are capable of forming inclusion complexes with perfume ingredients. Alpha-, beta-, and gamma-cyclodextrins can be obtained from, among others, American Maize-Products Company (Amaizo), Corn Processing Division, Hammond, Ind.; and Roquette Corporation, Gurnee, Ill. There are many derivatives of cyclodextrins that are known. Representative derivatives are those disclosed in U.S. Pat. No. : 3,426,011, Parmerter et al., issued Feb. 4, 1969; U.S. Pat. Nos. 3,453,257, 3,453,258, 3,453,259, and 3,453,260, all in the names of Parmerter et al., and all issued Jul. 1, 1969; U.S. Pat. No. 3,459,731, Gramera et al., issued Aug. 5, 1969; U.S. Pat. No. 3,553,191, Parmerter et al., issued Jan. 5, 1971; U.S. Pat. No. 3,565, 887, Parmerter et al., issued Feb. 23, 1971; U.S. Pat. No. 4,535,152, Szejtli et al., issued Aug. 13, 1985; U.S. Pat. No. 4,616,008, Hirai et al., issued Oct. 7, 1986; U.S. Pat. No. 4,638,058, Brandt et al., issued Jan. 20, 1987; U.S. Pat. No. 4,746,734, Tsuchiyama et al., issued May 24, 1988; and U.S. Pat. No. 4,678,598, Ogino et al., issued Jul. 7, 1987, all of said patents being incorporated herein by reference. Examples of cyclodextrin derivatives suitable for use herein are methyl-β-CD, hydroxyethyl-β-CD, and hydroxypropyl-β-CD of different degrees of substitution (D.S.), available from Amaizo and from Aldrich Chemical Company, Milwaukee, Wis. Water-soluble derivatives are also highly desirable.

The fragrance carriers comprising the fragrance-release complexes of the present invention can be incorporated into the personal cleansing bars as is or they can be encapsulated in, e.g., waxy materials, such as fatty acids.

If it is desired to encapsulate the fragrance carrier, the preferred coating materials include both water-insoluble and water-soluble materials, typically selected from waxy materials such as paraffinic waxes, microcrystalline waxes, animal waxes, vegetable waxes, saturated fatty acids and fatty alcohols having from 12 to 40 carbon atoms in their alkyl chain, and fatty esters such as fatty acid triglycerides, fatty acid esters of sorbitan and fatty acid esters of fatty alcohols, or from both water-insoluble and water-soluble polymers. Typical specific suitable waxy coating materials include lauric, myristic, palmitic, stearic, arachidic and behenic acids, stearyl and behenyl alcohol, microcrystalline wax, beeswax, spermaceti wax, candelilla wax, sorbitan tristearate, sorbitan tetralaurate, tripalmitin, trimyristin and octacosane. A preferred waxy material is coconut fatty acid.

Examples of polymeric materials which can be used for the coating of the particles herein are cellulose ethers such as ethyl, propyl or butyl cellulose; cellulose esters such as cellulose acetate, propionate, butyrate or acetate-butyrate; polyalkylene glycol such as ethylene, propylene, tetramethylene glycol; urea-formaldehyde resins, polyvinyl alcohol, polyvinyl chloride, polyvinylidene chloride, polyethylene, polypropylene, polyacrylates, polymethacrylates, polymethylmethacrylates and nylon. Such materials and their equivalents are described in greater detail in any conventional handbook of synthetic organic plastics, for example, in *Modern Plastics Encyclopaedia Volume*, Vol. 62, No. 10A (for 1985–1986) at pages 768–787, published by McGraw-Hill, New York, N.Y. (October 1985), incorporated herein by reference. A preferred polymeric material is ethyl cellulose. The polymeric coating materials can be plasticized with known plasticizing agents such as phthalate, adipate and sebacate esters, polyols (e.g., ethylene glycol), tricresyl phosphate, castor oil and camphor. These polymeric coatings are preferred for the superior protection they provide.

The coating when present, is generally present in an amount of from about 2% to about 50%, preferably from about 20% to about 40% by weight of the fragrance-releasing complex.

The coating material can comprise a mixture of waxy coating materials and polymeric coating materials. In such mixtures the waxy coating material will typically comprise from about 10% to about 90% of the mixture and the polymeric material about 10% to about 90%.

The function of the coating which surrounds the fragrance-releasing complex is to provide further improved stability, as well as to allow for dual delivery of fragrances wherein different fragrances can be impregnated in various complexes.

C. Impregnation of the Fragrance within the Carrier

At least a portion of the fragrance employed in the personal cleansing bar compositions of the present invention is impregnated within the hereinbefore-described fragrance carrier. To impregnate the fragrance within the fragrance carrier, the fragrance and the carrier are mixed together under shear conditions to provide a homogeneous mixture.

II. The Bar Carrier

In addition to the fragrance-releasing complex, the personal cleansing bar compositions of the present invention comprises from about 80% to about 99%, preferably from about 90% to about 99%, more preferably from about 95% to about 99% of a bar carrier. The bar carrier typically comprises a surfactant and water, in addition to other optional ingredients.

A. The Surfactant

The bar carrier of the present invention comprises from about 20% to about 99%, preferably from about 30% to about 90%, more preferably from about 40% to about 90% of a surfactant, which may include soap, synthetic surfactant, or a combination of both. The surfactant is typically present in the personal cleansing bar compositions of the present invention at levels ranging from about 20% to about 99%, preferably from about 30% to about 90%, more preferably from about 40% to about 80%.

Suitable synthetic surfactants include any surfactants known for use in personal cleansing bar compositions. For example, suitable synthetic surfactants can include surfactants selected from the group consisting of: anionic, nonionic, amphoteric and zwitterionic synthetic detergents. Both low and high lathering and high and low water-soluble surfactants can be used in the bar compositions of the present invention. Suds boosting synthetic detergent surfactants and/or synthetic detergent surfactants that are known as good dispersants for soap curds that are formed in hard water, are particularly desirable.

Examples include the water-soluble salts of organic, sulfonic acids and of aliphatic sulfuric acid esters, that is, water-soluble salts of organic sulfuric reaction products having in the molecular structure an alkyl radical of from 10 to 22 carbon atoms and a radical selected from the group consisting of sulfonic acid and sulfuric acid ester radicals.

Synthetic sulfate detergents of special interest are the normally solid alkali metal salts of sulfuric acid esters of normal primary aliphatic alcohols having from 10 to 22 carbon atoms. Thus, the sodium and potassium salts of alkyl sulfuric acids obtained from the mixed higher alcohols derived by the reduction of tallow or by the reduction of coconut oil, palm oil, palm kernel oil, palm oil stearin, babassu kernel oil or other oils of the lauric oil group can be used herein.

Other aliphatic sulfuric acid esters which can be suitably employed include the water-soluble salts of sulfuric acid esters of polyhydric alcohols incompletely esterified with high molecular weight soap-forming carboxylic acids. Such synthetic detergents include the water-soluble alkali metal salts of sulfuric acid esters of higher molecular weight fatty acid monoglycerides such as the sodium and potassium salts of the coconut oil fatty acid monoester of 1,2-hydroxypropane-3-sulfuric acid ester, sodium and potassium monomyristoyl ethylene glycol sulfate, and sodium and potassium monolauroyl diglycerol sulfate.

Some examples of good mild, lather-enhancing, synthetic detergent surfactants are, e.g., sodium lauroyl sarcosinate, alkyl glyceryl ether sulfonate (AGS), sulfonated fatty esters, and sulfonated fatty acids. Numerous examples of other surfactants are disclosed in the patents incorporated herein by reference. They include other alkyl sulfates, anionic acyl sarcosinates, methyl acyl taurates, N-acyl glutamates, acyl isethionates, alkyl sulfosuccinates, alkyl phosphate esters, ethoxylated alkyl phosphate esters, trideceth sulfates, protein condensates, mixtures of ethoxylated alkyl sulfates and alkyl amine oxides, betaines, sultaines, and mixtures thereof. Included in the surfactants are the alkyl ether sulfates with 1 to 12 ethoxy groups, especially ammonium and sodium lauryl ether sulfates.

Alkyl chains for these other surfactants are $C_8$–$C_{22}$, preferably $C_{10}$–$C_{18}$. Alkyl glycosides and methyl glucose esters are preferred mild nonionics which can be mixed with other mild anionic or amphoteric surfactants in the compositions of this invention. Alkyl polyglycoside detergents are useful lather enhancers.

Normally the soap/synthetic bars are prepared to contain a ratio of soap to synthetic detergent of from about 3:1 to about 25:1. The choice of suitable ratios will depend upon the particular synthetic detergent, the desired performance and physical characteristics of the finished bar, temperature, moisture and like processing considerations. A preferred ratio is from about 4:1 to about 7:1.

B. Water

The bar carrier employed in the personal cleansing bar compositions of the present invention typically comprise from about 1% to about 40%, preferably from about 5% to about 20% water. The personal cleansing bar compositions of the present invention typically comprise from about 1% to about 40%, preferably from about 5% to about 15% water.

C. Neat Fragrances

In addition to the fragrances impregnated within the fragrance carrier, the personal cleansing bar compositions of the present invention can also optionally contain fragrances present in their neat form (e.g., not impregnated within a fragrance carrier). Incorporating a neat fragrance into the personal cleansing bar compositions herein can contribute to unique fragrance impressions for the bar. For example, a personal cleansing bar composition which contains both a fragrance impregnated within a fragrance carrier and a neat fragrance can 1) give a dual fragrance impression (e.g., can exhibit different fragrance impressions for the dry(neat) bar versus the in-use bar), or 2) can optimize the fragrance impression for both the neat bar and the in-use bar.

The fragrances which can be used as neat fragrances for the personal cleansing bar compositions of the present invention are the same as those hereinbefore described for incorporation into the fragrance-releasing complex. The neat fragrance is typically present in an amount ranging from about 0.01% to about 10%, preferably from about 0.01% to about 2%, more preferably from about 0.1% to about 2% by weight of the bar carrier. The neat fragrance is typically present in an amount ranging from about 0.01% to about 10%, preferably from about 0.01% to about 2%, more preferably from about 0.1% to about 2% by weight of the personal cleansing bar compositions. The total fragrance (e.g., neat fragrance and fragrance incorporated into fragrance-releasing complex) typically present in the bar compositions of the present invention ranges from about 0.01 to about 10%, preferably from about 0.1 to about 5%, more preferably from about 0.4 to about 2%.

D. Other Optional Ingredients

The bar carrier employed in the personal cleansing bar compositions of the present invention can also include other optional ingredients. For example, the personal cleansing bars of the present invention can contain a polymeric skin mildness aid, such as those disclosed in the Small et al. and Medcalf et al. patents. (U.S. Pat. Nos. 4,673,525; 4,812,258; and 4,820,447 incorporated herein by reference.) The cationic synthetic polymers useful in the present invention are cationic polyalkylene imines, ethoxypolyalklene imines, and poly[N-[-3-(dimethylammonio)propyl]-N'-[3-(ethyleneoxyethylene dimethylammonio)propyl]urea dichloride] the latter of which is available from Miranol Chemical Company, Inc. under the trademark of Miranol A-15, CAS Reg. No. 68555-36-2.

Preferred cationic polymeric skin conditioning agents are those cationic polysaccharides of the cationic guar gum class with molecular weights of 1,000 to 3,000,000. More preferred molecular weights are from 2,500 to 350,000. These polymers have a polysaccharide backbone comprised of galactomannan units and a degree of cationic substitution ranging from about 0.04 per anhydroglucose unit to about 0.80 per anhydroglucose unit with the substituent cationic group being the adduct of 2,3-epoxypropyltrimethyl ammonium chloride to the natural polysaccharide backbone. Examples are JAGUAR C-14-S, C-15 and C-17 sold by the successor of the Celanese Corporation. Another preferred class of cationic polymeric skin conditioning agents are those cationic polysaccharides of the cationic cellulose class, such as JR 400, JR 30M and CR400 available from Amerchol.

The bar soap compositions of the present invention can contain other additives commonly included in toilet bars such as other fillers, sanitizing or antimicrobial agents, dyes, and the like.

Preservatives, e.g., sodium ethylenediaminetetraacetate (EDTA), generally at a level of less than 1% of the composition, can be incorporated in the cleansing products to prevent color and odor degradation. Antibacterial can also be incorporated, usually at levels up to 1.5%. The above patents disclose or refer to such ingredients and formulations which can be used in the bars of this invention, and are incorporated herein by reference.

Compatible salt and salt hydrates can be incorporated into the formulation. Some preferred salts are sodium chloride, sodium sulfate, disodium hydrogen phosphate, sodium pyrophosphate, sodium tetraborate. Sodium chloride is kept below 2.0% by weight of the bar, preferably less than 1%.

METHODS

1.) Tests for Hydrophilicity Of Carrier Particles

A fragrance carrier is considered to be hydrophilic for purposes herein if the carrier meets the criteria defined in either one of the following tests:

1. The visual Test

The visual test is based on visual observation of a fragrance-releasing complex comprising a fragrance carrier impregnated with a fragrance (e.g., perfume droplets) as it is released into a water solution.

A fragrance-releasing complex is first formed by adding 1 gram of water-insoluble fragrance (e.g., perfume oil) to the inorganic fragrance carrier at a ratio of fragrance:fragrance carrier ranging from 5:1 to 1:10, with stirring until all of the fragrance is absorbed into the fragrance carrier. The particular ratio of fragrance:fragrance carrier employed test depends on the absorbency of the fragrance carrier. When a fragrance carrier with a high absorbency is used, the ratio of fragrance:fragrance carrier is about 5:1. When a carrier of low absorbency is used, the ratio of fragrance:fragrance carrier is about 1:10. For fragrance carriers with moderate absorbencies, the ratio of fragrance:fragrance carrier lies between 5:1 and 1:10. Typical ratios of fragrance:fragrance carrier for certain key fragrance carriers are listed in the table below:

| Fragrance Carrier | Ratio Fragrance:Fragrance Carrier |
|---|---|
| Silica | 2:1 |
| Zeolite | 1:6 |
| β-Cyclodextrin | 1:6 |

Once all of the fragrance has been absorbed by the fragrance carrier, the fragrance-releasing complex is allowed to equilibrate overnight in a sealed vial. Fifty (50) ml of distilled water is then added to the complex with stirring at room temperature. The hydrophilic fragrance particles are defined as those particles which release a noticeable amount of fragrance in the water solution when the fragrance-releasing complex is mixed with the water.

2. The Sniffing Test

The second hydrophilicity test is based on sniffing the headspace of the dry and wet fragrance-releasing complex comprising the fragrance carrier impregnated with the fragrance.

A fragrance-releasing complex is prepared as hereinbefore described for the Visual Test. One gram of the fragrance releasing complex is set aside. One (1) gram of the fragrance releasing complex is added to 1 ml of water. The dry fragrance-releasing complex is then compared to the wet fragrance-releasing complex. When there is a noticeable difference in the perfume intensity between the wet complex and the dry complex, the fragrance carrier particles are considered to be "hydrophilic" for purposes herein.

EXAMPLES

The following examples and formulas are illustrative and are not intended to limit the scope of the invention. The methods of making milled bars are well known. All levels and ranges, temperatures, results, etc., used herein are approximations unless otherwise specified.

Example 1

A Silica-Perfume fragrance-releasing complex is prepared by slowly adding Perfume A into Silica powder in a kitchen blender at a weight ratio of Silica:perfume at 1:2. The Silica is SYLOID 244FP Silica gel from Grace Davison Chemical Division. The Perfume A is comprised mainly of highly and moderately volatile perfume components which provide fresh/clean impression. Some of the major ingredients of Perfume A are: Benzyl Acetate, Ethyl Aceto Acetate, Ethyl-2-Methyl Butyrate, P. T. Bucinal, and Phenoxy Ethyl Iso Butyrate, etc.

| Composition of Silica-Perfume Fragrance-Releasing Complex | |
|---|---|
| Ingredient | Wt. % |
| SYLOID 244FP Silica Gel | 33 |
| Perfume A | 67 |

A Control Bar is made by mixing neat perfume A directly into dried soap noodles in an amalgamator. The material is milled several times in a 3-roll soap mill to obtain a homogeneous mixture of perfume and soap flakes. Then the material is processed on a plodder and is stamped into a soap bar.

A Test Bar is made by mixing the Silica-Perfume A fragrance-releasing complex into dried soap noodles in an amalgamator. After the mixture is processed through a 3-roll mill and a plodder, it is stamped into a soap bar.

The final bar composition of the Control Bar and the Test Bar are listed in the following table.

TABLE I

Composition of Control and Test Bars

| Composition | Control Bar | Test Bar |
|---|---|---|
| Soap | 80.24 | 79.84 |
| Free Fatty Acid | 5.73 | 5.70 |
| Water | 11.56 | 11.50 |
| NaCl | 1.11 | 1.10 |
| $TiO_2$ | 0.25 | 0.25 |
| Perfume A | 1.00 | 1.00 |
| SYLOID Silica | — | 0.50 |
| Misc. | 0.11 | 0.11 |

Both soap bars are placed in a stability room at 120° F. for 10 days. The control bar is not stable in terms of color or odor. Therefore, the control bar is not acceptable as a commercial personal cleansing bar. The test bar shows significantly improved color and odor stability. The test bar is acceptable as a commercial personal cleansing bar.

Example 2

A Silica-Perfume fragrance-releasing complex is first prepared by slowing adding perfume A into Silica in a kitchen blender at a weight ratio of Silica:Perfume at 1:1. The Silica is SYLOID 244FP Silica gel from Grace Davison Chemical Division. The Silica-Perfume fragrance-releasing complex is then coated with melten coconut fatty acid (FA) at 120° F.. The coated silica-perfume particle has a weight ratio of silica:perfume:FA at 1: 1: 1. The coated particle has very low perfume odor.

Composition of Coated Silica-Perfume Fragrance-Releasing Complex

| Ingredient | Wt. % |
|---|---|
| SYLOID 244FP Silica Gel | 33.3 |
| Perfume A | 33.3 |
| Coconut Fatty Acid | 33.3 |

Two control bars are made: (1) Control Bar I contains 0.4% Perfume A and 0.9% Perfume B as neat oil in the soap matrix; (2) control bar II contains 0.9% perfume B only. A test bar is made by first adding the coated silica-perfume fragrance-releasing complex in the soap matrix, then mixing neat perfume B into composition. The perfume levels in the test bars are: 0.4% perfume A and 0.9% perfume B. The compositions of both test bars and control bar are listed in Table II.

TABLE II

Composition of Control and Test Bars

| Composition | Control Bar I | Control Bar II | Test Bar |
|---|---|---|---|
| Soap | 80.01 | 80.34 | 79.68 |
| Free Fatty Acid | 5.71 | 5.73 | 5.69 |
| Water | 11.52 | 11.57 | 11.47 |
| NaCl | 1.10 | 1.10 | 1.10 |
| $TiO_2$ | 0.25 | 0.25 | 0.25 |
| Perfume A | 0.40 | — | 0.40 |
| Perfume B | 0.90 | 0.90 | 0.90 |
| SYLOID Silica | — | — | 0.40 |
| Coconut Fatty Acid | — | — | 0.40 |
| Misc. | 0.11 | 0.11 | 0.11 |

The dry bar fragrance of the Test Bar is very similar to that of Control Bar II. However, the wet bar fragrance of the Test Bar approaches that of Control Bar I. This demonstrates that perfume is entrapped in the coated particle. The perfume is released during the product usage.

Example 3

A Cyclodextrin-Perfume fragrance-releasing complex is prepared by the following method: 85 g of Beta Cyclodextrin (β-CD) is mixed in 750 ml of water. The solution is placed on a magnetic stir/hot plate. The solution is heated to 160° F. with stirring. After the solution is clear, 15 g of perfume C is slowly added in the β-CD solution. The solution immediately becomes cloudy. Stirring and heating is continued for about 2 more hours after addition of Perfume C. The solution is kept untouched overnight while the perfume-CD complex precipitates during cooling. The precipitate is filtered and dried in vacuo. The resulting CD-Perfume C fragrance-releasing complex has low perfume odor.

Composition of CD-Perfume Fragrance-Releasing Complex

| Ingredient | Wt. % |
|---|---|
| β-Cyclodextrin | 85 |
| Perfume C | 15 |

The β-CD-Perfume C powder is added into the dry soap matrix. Then, a neat perfume D is added. The finished bar contains about 1.0% Perfume C and 0.8% Perfume D. The complete composition of the test bar is listed in Table III.

TABLE III

Composition of Test Bar

| Composition | Test Bar |
|---|---|
| Surfactant | 61.7 |
| Paraffin | 15.83 |
| Water | 5.14 |
| $Na_2SO_4$ | 0.80 |
| NaCl | 0.48 |
| $TiO_2$ | 0.25 |
| Preservative | 0.10 |
| Etidornate | 0.10 |
| Glycerin | 8.10 |
| Polyox | 0.03 |
| Perfume C | 1.00 |
| Perfume D | 0.80 |
| β-CD | 5.67 |

The dry bar fragrance is mainly perfume D. The in-use fragrance changes to mainly perfume C. This indicates that perfume in entrapped in the test bar when the test bar is dry. The perfume is released by water during use.

Example 4

A Zeolite-Perfume fragrance-releasing complex is prepared by slowly adding perfume E into Zeolite at a Zeolite::Perfume ratio of 6:1. The Zeolite is SYLOSIV A10 from Grace Davison Chemical Division.

| Composition of Zeolite-Perfume Fragrance-Releasing Complex | |
|---|---|
| Ingredient | Wt. % |
| Zeolite SYLOSIV A10 | 85.71 |
| Perfume E | 14.29 |

The control bar is made by directly mixing Perfume E into the soap mix. The test bar is made by mixing the Zeolite-Perfume E fragrance-releasing complex into the soap matrix. The perfume level in both bars is at 1.3%. The compositions of both bars are listed in Table IV.

TABLE IV

| Composition of Control and Test Bars | | |
|---|---|---|
| Composition | Control Bar | Test Bar |
| Soap | 80.04 | 73.69 |
| Free Fatty Acid | 5.73 | 5.28 |
| Water | 11.46 | 10.55 |
| NaCl | 1.11 | 1.02 |
| $TiO_2$ | 0.25 | 0.25 |
| Perfume D | 1.30 | 1.30 |
| SYLOSIV A10 Zeolite | — | 7.80 |
| Misc. | 0.11 | 0.11 |

The dry bar perfume impact of the test bar is much lower than that of the control bar. However, the wet-bar perfume impact of the test bar is very similar to that of the control bar. This shows that the perfume remains entrapped in the Zeolite when the product is dry. The perfume is released when the product is wet.

What is claimed is:

1. A personal cleansing bar composition having desirable fragrance delivery comprising:
   a) from about 0.1% to about 20% of a fragrance-releasing complex which comprises:
      i) from about 10% to about 90% of a hydrophilic inorganic porous fragrance carrier; and
      ii) from about 10% to about 90% of a fragrance impregnated within said carrier, wherein the ratio of the fragrance:fragrance carrier ranges from about 5:1 to about 1:10; and
   b) from about 80% to about 99% of a bar carrier.

2. The personal cleansing bar composition of claim 1 wherein the bar carrier comprises:
   a) from about 20% to about 99% surfactant; and
   b) from about 1% to about 40% water.

3. The personal cleansing bar composition of claim 2 comprising:
   a) from about 0.1% to about 20% of the fragrance-releasing complex which comprises:
      i) flora about 10% to about 90% of the hydrophilic inorganic porous fragrance carrier; and
      ii) from about 10% to about 90% of the fragrance impregnated within said carrier; and
   b) from about 80% to about 99% of the bar carrier.

4. The personal cleansing bar composition of claim 2 wherein the fragrance carrier comprises carriers selected from the group consisting of amorphous silicas, precipitated silicas, fumed silicas and mixtures thereof, wherein the carrier has a particle size of less than about 50 microns and a pore volume of at least 0.1 ml/g consisting of pores with a diameter ranging from about 4 to about 100 Å.

5. The personal cleansing bar composition of claim 2 wherein the fragrance carrier comprises a carrier selected from the group consisting of zeolite, alumina and mixtures thereof, wherein the carrier has a particle size of less than about 50 microns and a pore volume of at least 0.1 ml/g consisting of pores with a diameter ranging from about 4 to about 100 Å.

6. The personal cleansing bar composition of claim 2 wherein the fragrance carrier comprises cyclodextrin selected from the group consisting of alpha-cyclodextrin; beta-cyclodextrin; gamma-cyclodextrin; and mixtures and derivatives thereof.

7. The personal cleansing bar composition of claim 2 wherein the fragrance is selected from the group consisting of perfume ingredients, cooling agents, and mixtures thereof.

8. The personal cleansing bar composition of claim 2 wherein at least a portion of the fragrance is not stable in a personal cleansing bar composition when used as a neat fragrance due to its high volatility and is selected from the group consisting of: highly volatile perfume components having a boiling point up to about 250° C.; moderately volatile perfumes components having a boiling point from about 250° C. to about 350° C.; and mixtures thereof.

9. The personal cleansing bar composition of claim 2 wherein at least a portion of the fragrance is not stable in a personal cleansing bar composition when used as a neat fragrance due to discoloration or odor character changes or perfume intensity changes of the personal cleansing bar composition.

10. The personal cleansing bar composition of claim 2 which additionally comprises from about 0.01% to about 10% of neat fragrance.

11. The personal cleansing bar of claim 2 wherein the fragrance is encapsulated with a coating material selected from the group consisting of paraffin waxes, microcrystalline waxes, animal waxes, vegetable waxes, saturated fatty acids and fatty alcohols, fatty esters, cellulose esters, polyalkylene glycol, polyvinyl alcohol, and mixtures thereof and wherein the coating material is present in an amount ranging from about 2% to about 50% of the fragrance-releasing complex.

12. The personal cleansing bar of claim 4 wherein the fragrance is encapsulated with a coating material selected from the group consisting of paraffin waxes, microcrystalline waxes, animal waxes, vegetable waxes, saturated fatty acids and fatty alcohols, fatty esters, cellulose esters, polyalkylene glycol, polyvinyl alcohol, and mixtures thereof and wherein the coating material is present in an amount ranging from about 2% to about 50% of the fragrance-releasing complex.

13. The personal cleansing bar of claim 5 wherein the fragrance is encapsulated with a coating material selected from the group consisting of paraffin waxes, microcrystalline waxes, animal waxes, vegetable waxes, saturated fatty acids and fatty alcohols, fatty esters, cellulose esters, polyalkylene glycol, polyvinyl alcohol, and mixtures thereof and wherein the coating material is present in an amount ranging from about 2% to about 50% of the fragrance-releasing complex.

14. The personal cleansing bar of claim 6 wherein the fragrance-releasing complex is encapsulated with a coating material selected from the group consisting of paraffin waxes, microcrystalline waxes, animal waxes, vegetable waxes, saturated fatty acids and fatty alcohols, fatty esters, cellulose esters, polyalkylene glycol, polyvinyl alcohol, and mixtures thereof and wherein the coating material is present in an amount ranging from about 2% to about 50% of the fragrance-releasing complex.

15. The personal cleansing bar composition of claim 10 wherein the fragrance impregnated into the fragrance carrier has the same character as the neat fragrance for optimum fragrance display in both the neat personal cleansing bar composition and in the personal cleansing bar composition during use.

16. The personal cleansing bar composition of claim 10 wherein the fragrance impregnated into the fragrance carrier has a different character compared to the neat fragrance to provide a personal cleansing bar having dual fragrance characteristics.

17. The personal cleansing bar composition of claim 2 which are prepared according to the following process:
 a) mixing the fragrance and the fragrance carrier to provide a fragrance-releasing complex; and
 b) mixing the fragrance-releasing complex into dried soap noodles to provide the personal cleansing bar composition.

18. The personal cleansing bar composition of claim 17 wherein the fragrance-releasing complex is encapsulated with a coating material selected from the group consisting of paraffin waxes, microcrystalline waxes, animal waxes, vegetable waxes, saturated fatty acids and fatty alcohols, fatty esters, cellulose esters, polyalkylene glycol, polyvinyl alcohol, and mixtures thereof.

19. The personal cleansing bar composition of claim 2 which are prepared according to the following process:
 a) mixing the fragrance and the fragrance carrier to provide a fragrance-releasing complex;
 b) mixing the fragrance-releasing complex into dried soap noodles; and
 c) mixing in a neat fragrance to provide the personal cleansing bar composition.

20. The personal cleansing bar composition of claim 19 wherein the fragrance-releasing complex is encapsulated with a coating material selected from the group consisting of paraffin waxes, microcrystalline waxes, animal waxes, vegetable waxes, saturated fatty acids and fatty alcohols, fatty esters, cellulose esters, polyalkylene glycol, polyvinyl alcohol, and mixtures thereof.

* * * * *